US010571323B2

(12) United States Patent
Werbach et al.

(10) Patent No.: US 10,571,323 B2
(45) Date of Patent: Feb. 25, 2020

(54) ELECTRICAL CONFIGURATION FOR A VIBRATING METER

(71) Applicant: Micro Motion, Inc., Boulder, CO (US)

(72) Inventors: Christopher A Werbach, Longmont, CO (US); Allan L Samson, Fort Luptom, CO (US)

(73) Assignee: Micro Motion, Inc., Boulder, CO (US)

( * ) Notice: Subject to any disclaimer, the term of this patent is extended or adjusted under 35 U.S.C. 154(b) by 330 days.

(21) Appl. No.: 14/827,536

(22) Filed: Aug. 17, 2015

(65) Prior Publication Data
US 2015/0355008 A1   Dec. 10, 2015

Related U.S. Application Data

(62) Division of application No. 14/125,246, filed as application No. PCT/US2011/043156 on Jul. 7, 2011, now Pat. No. 9,200,937.

(51) Int. Cl.
*G01F 1/84*     (2006.01)
*G01F 15/18*    (2006.01)
*G01N 9/00*     (2006.01)

(52) U.S. Cl.
CPC .......... *G01F 1/8468* (2013.01); *G01F 1/8404* (2013.01); *G01F 1/8409* (2013.01); *G01F 15/18* (2013.01); *G01N 9/002* (2013.01); *Y10T 29/49117* (2015.01); *Y10T 29/49119* (2015.01)

(58) Field of Classification Search
CPC ...... H05K 1/189; H05K 1/028; H05K 1/0281; H05K 2201/10083; H05K 1/0265; H05K 2201/0979; H05K 3/326; H05K 3/361; H05K 3/4635; H05K 3/4691; H05K 2201/05–058; H05K 2201/052; H05K 2201/053; H01R 12/772; G01F 1/845–8495; G01F 1/8409; G01F 15/18
See application file for complete search history.

(56) References Cited

U.S. PATENT DOCUMENTS

| 4,036,578 | A | * | 7/1977 | Herman | F21K 5/02 |
| | | | | | 362/13 |
| 4,876,898 | A | | 10/1989 | Cage et al. | |
| 5,349,872 | A | | 9/1994 | Kalotay et al. | |
| 5,584,704 | A | * | 12/1996 | Romann | F02M 51/005 |
| | | | | | 439/130 |
| 5,669,775 | A | * | 9/1997 | Campbell | H01R 23/661 |
| | | | | | 361/761 |

(Continued)

FOREIGN PATENT DOCUMENTS

| EP | 0553939 A2 | * | 8/1993 | .......... G01F 1/8409 |
| EP | 1001254 A1 | | 5/2000 | |
| JP | 09250940 A | | 9/1997 | |

*Primary Examiner* — Livius R. Cazan
(74) *Attorney, Agent, or Firm* — The Ollila Law Group LLC (57) ABSTRACT

A method for assembling a sensor assembly is provided. The method includes positioning one or more conduits within a case, and coupling one or more sensor components to the one or more conduits, with the sensor components including one or more of a driver, a first pick-off sensor, and a second pick-off sensor. A flexible circuit is positioned within the case, one or more sensor component flexures are coupled to extend from a body of the flexible circuit to a sensor component of the one or more sensor components.

6 Claims, 6 Drawing Sheets

(56) References Cited

U.S. PATENT DOCUMENTS

| | | | | |
|---|---|---|---|---|
| 5,717,556 A | * | 2/1998 | Yanagida | H05K 1/0278 |
| | | | | 174/254 |
| 6,307,751 B1 | * | 10/2001 | Bodony | G06F 1/16 |
| | | | | 361/679.08 |
| 2007/0077805 A1 | * | 4/2007 | Nomura | G03B 17/04 |
| | | | | 439/331 |

* cited by examiner

ELECTRICAL CONFIGURATION FOR A VIBRATING METER

CROSS-REFERENCE TO RELATED APPLICATIONS

This Application is a divisional of application Ser. No. 14/125,246, filed Dec. 10, 2013, which is the National Stage of International Application No. PCT/US2011/043156, filed Jul. 7, 2011.

TECHNICAL FIELD

The embodiments described below relate to, vibrating meters, and more particularly, to an improved electrical configuration method for a vibrating meter.

BACKGROUND OF THE INVENTION

Vibrating meters, such as for example, vibrating densitometers and Coriolis flow meters are generally known and are used to measure mass flow and other information for materials within a conduit. The meter comprises a sensor assembly and an electronics portion. The material within the sensor assembly may be flowing or stationary. Each type of sensor may have unique characteristics, which a meter must account for in order to achieve optimum performance.

Exemplary Coriolis flow meters are disclosed in U.S. Pat. Nos. 4,109,524, 4,491,025, and Re. 31,450 all to J. E. Smith et al. These flow meters have one or more conduits of straight or curved configuration. Each conduit configuration in a Coriolis mass flow meter has a set of natural vibration modes, which may be of simple bending, torsional, or coupled type. Each conduit can be driven to oscillate at a preferred mode.

Figure 1:
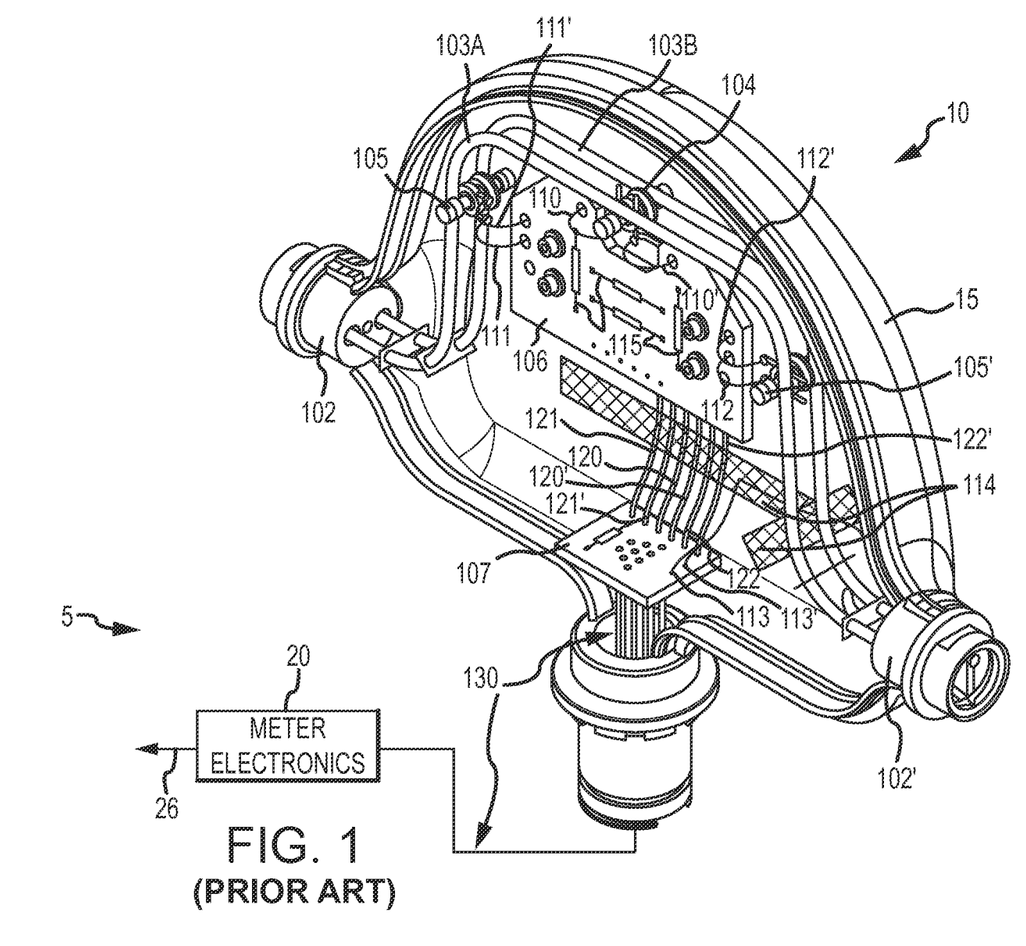
FIG. 1 shows a prior art sensor assembly.

FIG. 1 shows a prior art sensor assembly 10. The sensor assembly 10 is typically in electrical communication with a meter electronics 20 to form a vibrating meter 5. While the sensor assembly 10 is described below as comprising a portion of a Coriolis flow meter, it should be appreciated that the sensor assembly 10 could just as easily be utilized as another type of vibrating meter. The sensor assembly 10 receives a flowing fluid; however, sensor assemblies of vibrating meters are not necessarily limited to a structure where a fluid under test is flowing. Therefore, the sensor assembly 10 may comprise the vibrating portion of a vibrating densitometer where the fluid is not flowing, the sensing portion of ultra-sonic flow meters, the sensing portion of magnetic volumetric flow meters, etc.

The meter electronics can be connected to the sensor assembly 10 to measure one or more characteristics of a flowing material, such as, for example, density, mass flow rate, volume flow rate, totalized mass flow, temperature, and other information.

The front half of the sensor assembly's case 15 is removed in FIG. 1 to show the interior components. The sensor assembly 10 includes a pair of flanges 101 and 101', manifolds 102 and 102', and conduits 103A and 103B. Manifolds 102, 102' are affixed to opposing ends of the conduits 103A and 103B. The conduits 103A and 103B extend outwardly from the manifolds in an essentially parallel fashion. When the sensor assembly 10 is inserted into a pipeline system (not shown) which carries the flowing material, the material enters sensor assembly 10 through the flange 101, passes through the inlet manifold 102 where the total amount of material is directed to enter conduits 103A, 103B, flows through the conduits 103A, 103B and back into the outlet manifold 102' where it exits the sensor assembly 10 through the flange 101'.

The sensor assembly 10 can include a driver 104. The driver 104 is shown affixed to conduits 103A, 103B in a position where the driver 104 can vibrate the conduits 103A, 103B in the drive mode, for example. The driver 104 may comprise one of many well-known arrangements such as a coil mounted to the conduit 103A and an opposing magnet mounted on the conduit 103B. A drive signal in the form of an alternating current can be provided by the meter electronics 20, such as for example via first and second wire leads 110, 110', and passed through the coil to cause both conduits 103A, 103B to oscillate about bending axes W-W and W'-W'. The wire leads 110 and 110' are coupled to the driver 104 and a first printed circuit board (PCB) 106. Generally the wire leads are coupled to the first PCB 106 and the driver 104 by soldering. A second set of wire leads 120 and 120' couple the first PCB to a second PCB 107. The second PCB 107 is in electrical communication with the meter electronics via leads 130. The prior art electrical configuration for the driver 104 shown requires four wire leads and two PCBs 106 and 107, resulting in eight soldered joints prior to exiting the sensor assembly's case 15.

The sensor assembly 10 also includes a pair of pick-off sensors 105, 105' that are affixed to the conduits 103A, 103B. According to an embodiment, the pick-off sensors 105, 105' may be electromagnetic detectors, for example, pick-off magnets and pick-off coils that produce sensor signals that represent the velocity and position of the conduits 103A, 103B. For example, the pick-off sensors 105, 105' may supply pick-off signals to the meter electronics 20 via pathways 111, 111', 112, and 112', which provide an electrical communication path between the pick-off sensors 105, 105' and the first PCB 106. A second set of wire leads 121, 121', 122, and 122' provide electrical communication between the first and second PCBs 106 and 107 for the pick-off sensors 105, 105'. Therefore, the electrical configuration requires eight wire leads for a total of sixteen solder joints for the pick-off sensors 105, 105' prior to exiting the sensor assembly's case 15. The power to/from the driver 104 and pick-off sensors 105, 105' can be regulated using resistors 115, which are shown coupled to the first PCB 106.

Additionally shown are wire leads 113, 113' for a temperature sensing device such as a resistance temperature detector (RTD) (not shown) that is coupled to the second PCB 107. In some prior art sensor assemblies, the wire leads are also held to the case 15 by tape 114 or some other adhering means to restrict the movement of the leads irrespective of the sensor assembly's orientation.

Those of ordinary skill in the art will appreciate that the motion of the conduits 103A, 103B is proportional to certain characteristics of the flowing material, for example, the mass flow rate and the density of the material flowing through the conduits 103A, 103B.

According to an embodiment, the meter electronics receives the pick-off signals from the pick-off sensors 105, 105'. A path 26 can provide an input and an output means that allows one or more meter electronics 20 to interface with an operator. The meter electronics 20 can measure one or more characteristics of the fluid under test such as, for example, a phase difference, a frequency, a time delay (phase difference divided by frequency), a density, a mass flow rate, a volume flow rate, a totalized mass flow, a temperature, a meter verification, and other information as is generally known in the art.

For example, as material flows into the sensor assembly 10 from a connected pipeline on the inlet side of the sensor assembly 10, it is directed through the conduit 103A, 103B, and exits the sensor assembly 10 through the outlet side of the sensor. The natural vibration modes of the vibrating material filled system are defined in part by the combined mass of the conduits and the material flowing within the conduits.

When there is no flow through the sensor assembly, a driving force applied to the conduits 103A, 103B by the driver 104 causes all points along the conduits 103A, 103B to oscillate with identical phase or small "zero offset," which is a time delay measured at zero flow. As material begins to flow through the sensor assembly, Coriolis forces cause each point along the conduit(s) to have a different phase. For example, the phase at the inlet end of the sensor lags the phase at the centralized driver position, while the phase at the outlet leads the phase at the centralized driver position. Pick-off sensors 105, 105' on the conduits 103A, 103B produce sinusoidal signals representative of the motion of the conduits 103A, 103B. Signals output from the pick-off sensors 105, 105' are processed to determine the phase difference between the pick-off sensors 105, 105'. The phase difference between the two or more pick-off sensors 105, 105' is proportional to the mass flow rate of the material flowing through the conduits 103A, 103B.

The mass flow rate of the material can be determined by multiplying the phase difference by a Flow Calibration Factor (FCF). Prior to installation of the sensor assembly 10 of the flow meter into a pipeline, the FCF is determined by a calibration process. In the calibration process, a fluid is passed through the flow conduits 103A, 103B at a known flow rate and the relationship between the phase difference and the flow rate is calculated (i.e., the FCF). The sensor assembly 10 of the flow meter 5 subsequently determines a flow rate by multiplying the FCF by the phase difference of the pick-off sensors 105, 105'. In addition, other calibration factors can be taken into account in determining the flow rate.

Due, in part, to the high accuracy of vibrating meters, and Coriolis flow meters in particular, vibrating meters have seen success in a wide variety of industries. However, as mentioned above, the sensor assembly's electrical configuration to communicate with the driver 104 and pick-off sensors 105, 105' requires an excessive number of wire leads and solder joints. The solder joint typically restricts the temperature range the sensor assembly is capable of handling. Further because each wire lead is typically cut and soldered individually by hand, sensor assemblies are subject to wide variability from one sensor assembly to another. Another problem with the prior art electrical configuration is that the wire leads from the first PCB 106 to the driver 104 and pick-off sensors 105, 105' are subject to an excessive amount of strain that often leads to premature failure. If a single wire lead breaks, the entire sensor assembly 10 is typically rendered inoperable.

The embodiments described below overcome these and other problems and an advance in the art is achieved. The embodiments described below provide an improved electrical configuration for a sensor assembly that results in a cheaper, more efficient, and more reliable sensor assembly. The improved sensor assembly utilizes a flexible circuit rather than a rigid PCB with various wire leads. Additionally, in some embodiments, the flexible circuit can withstand higher temperatures than the prior art wire leads that are soldered to the sensor components.

SUMMARY OF THE INVENTION

A method for assembling a sensor assembly is provided according to an embodiment. The method comprises steps of positioning one or more conduits within a case and coupling one or more sensor components to the one or more conduits, the sensor components including one or more of a driver, a first pick-off sensor, and a second pick-off sensor. According to an embodiment, the method further comprises a step of positioning a flexible circuit within the case. According to an embodiment, the method further comprises a step of coupling one or more sensor component flexures extending from a body of the flexible circuit to a sensor component of the one or more sensor components.

ASPECTS

According to an aspect, a method for assembling a sensor assembly comprises steps of:
  positioning one or more conduits within a case;
  coupling one or more sensor components to the one or more conduits, the sensor components including one or more of a driver, a first pick-off sensor, and a second pick-off sensor;
  positioning a flexible circuit within the case; and
  coupling one or more sensor component flexures extending from a body of the flexible circuit to a sensor component of the one or more sensor components.

Preferably, the method further comprises coupling the flexible circuit to a meter electronics to provide electrical communication between the meter electronics and the one or more sensor components.

Preferably, the step of coupling the one or more sensor component flexures comprises inserting a sensor component pin extending from a sensor component into a coupling aperture formed in the sensor component flexure.

Preferably, the method further comprises a step of coupling a sensor component flexure to a strain relief such that a portion of the sensor component flexure coupled to the strain relief and the coupling aperture remain substantially stationary with respect to one another during vibration of the one or more conduits.

Preferably, the strain relief is coupled to a sensor component.

Preferably, the strain relief comprises a plate and the step of coupling the sensor component flexure to the strain relief comprises positioning a portion of the sensor component flexure between the plate and a conduit bracket of the sensor component.

Preferably, the method further comprises a step of inserting a tubular rivet into each of the coupling apertures formed in the sensor component flexure.

Preferably, the method further comprises a step of coupling the tubular rivet to the sensor component pin.

Preferably, each of the sensor component flexures comprises one or more electrical traces.

Preferably, the flexible circuit further comprises a redundant flexure coupled to the at least one sensor component flexure.

Preferably, each of the sensor component flexures comprises a primary electrical trace and a redundant electrical trace.

DETAILED DESCRIPTION OF THE INVENTION

FIGS. 2-7 and the following description depict specific examples to teach those skilled in the art how to make and use the best mode of embodiments of a sensor assembly. For the purpose of teaching inventive principles, some conventional aspects have been simplified or omitted. Those skilled in the art will appreciate variations from these examples that fall within the scope of the present description. Those skilled in the art will appreciate that the features described below can be combined in various ways to form multiple variations of the sensor assembly. As a result, the embodiments described below are not limited to the specific examples described below, but only by the claims and their equivalents.

Figure 2:
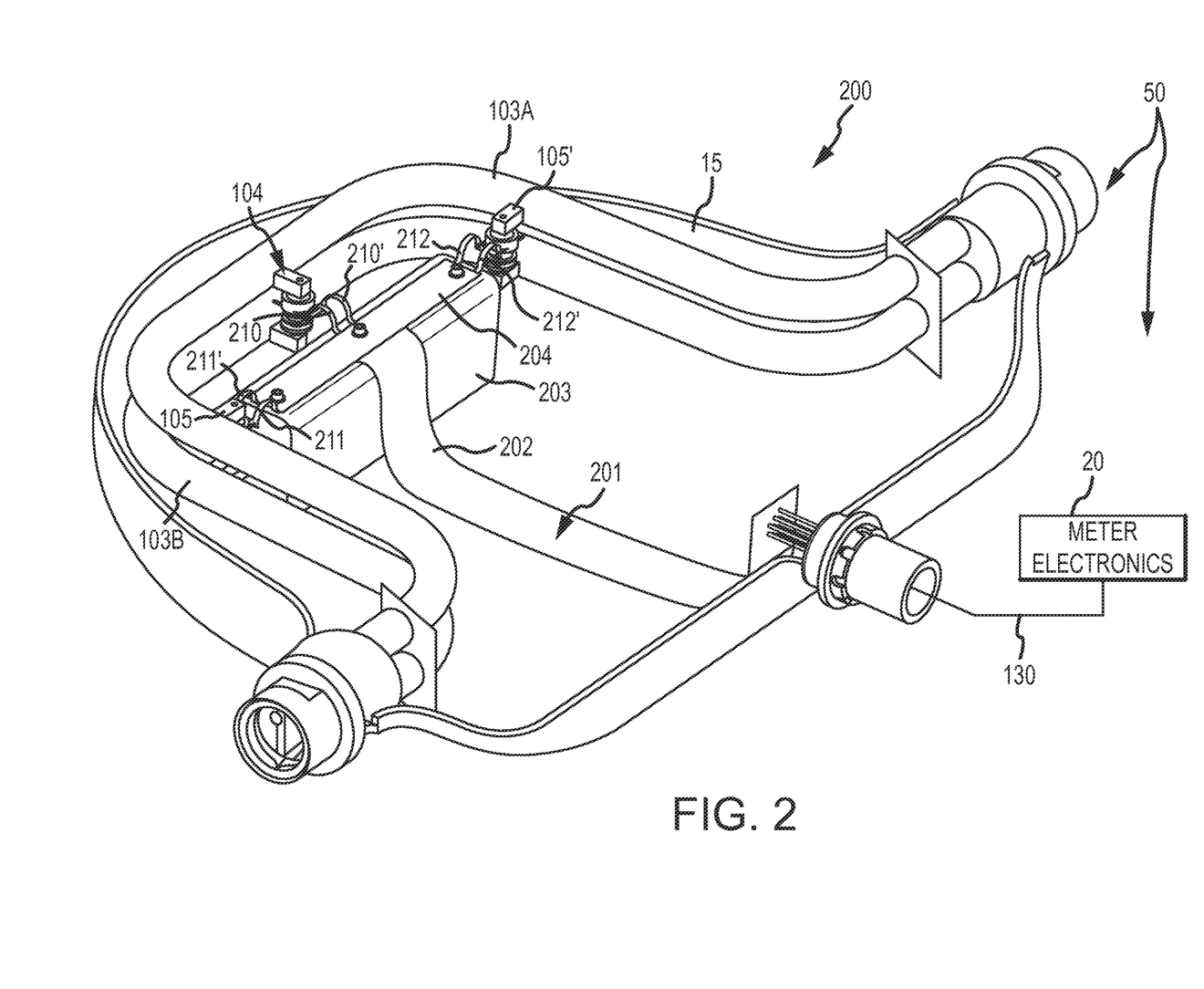
FIG. 2 shows a sensor assembly for a vibrating meter according to an embodiment.

FIG. 2 shows a vibrating meter 50 including the meter electronics 20 and a sensor assembly 200 according to an embodiment. Common reference numbers are used for components of the sensor assembly 200 that also comprise components of the prior art sensor assembly 10. The embodiment shown in FIG. 2 has the front half of the case 15 removed in order to illustrate the interior components. As shown, the sensor assembly 200 has eliminated both the first and second PCBs 106, 107 as well as the wire leads. Rather, the sensor components are coupled to a flexible circuit 201, sometimes referred to in the art as "flex circuit." According to an embodiment, the sensor components are in electrical communication with the meter electronics 20 via the flexible circuit 201. The sensor components may include one or more of the driver 104, the pick-off sensors 105, 105', and the RTD (not shown), for example. According to an embodiment, the flexible circuit 201 can be formed as a one-piece component. The flexible circuit 201 can include a main body 202 and one or more sensor component flexures 210-212' extending from the main body 202. The flexible circuit 201 can communicate between the leads 130 and the sensor components. Therefore, in some embodiments, the flexible circuit 201 can be coupled to the plurality of leads 130. The leads 130 can provide an electrical communication path between the flexible circuit 201 and the meter electronics 20, for example. Alternatively, the leads 130 may be eliminated and the flexible circuit 201 may extend out of the case 15 to the meter electronics 20. Therefore, the flexible circuit 201 provides electrical communication between the sensor components and devices external to the sensor assembly 200, such as the meter electronics 20. Consequently, the flexible circuit 201 has replaced the wire leads 110-122' along with the two PCBs 106, 107 of the prior art sensor assembly 10.

According to an embodiment, the flexible circuit 201 can comprise a flexible flat cable, a ribbon cable, etc. The flexible circuit 201 may comprise one or more thin, flexible, insulating substrates, such as polyethylene, Polyethylene terephthalate (PET), or some other plastic or insulating material well-known in the art. The flexible circuit 201 can comprise a plurality of electrical traces (See FIGS. 5 & 6). The electrical traces may be contained within two insulating flexible substrates, i.e., sandwiched between two layers of the flexible substrate. A common example of a flexible circuit is known with metallic traces bonded, laminated, etched, etc. to a flat and flexible plastic substrate. The metallic traces may comprise copper films, photo-etched or plated copper films, or some other material generally known in the art that can be used as an electrical trace to carry power, signals, and/or ground. The particular configuration of the flexible circuit 201 may vary depending upon the number of electrical traces required and the particular configuration. Therefore, the specific configuration shown in FIG. 2 should in no way limit the scope of the present embodiment.

Unlike a rigid PCB, the flexible circuit 201 is resilient and can deform or otherwise flex to accommodate various configurations. The flexible circuit 201 can therefore, relieve a substantial amount of stress seen in the prior art electrical configuration.

According to an embodiment, the sensor assembly 200 can further include a mounting block 203. According to an embodiment, at least a portion of the flexible circuit 201 can be mounted on the mounting block 203. More specifically, a portion of the main body 202 of the flexible circuit 201 can be mounted on the mounting block 203. The flexible circuit 201 can be retained on the mounting block 203 using a mounting plate 204 or similar device. According to an embodiment, a portion of the main body 202 can be mounted on the mounting block 203 in order to substantially center the flexible circuit 201 with respect to the case 15, for example. For example, the mounting block 203 can be provided to center a portion of the flexible circuit 201 between the two conduits 103A, 103B.

According to an embodiment, the flexible circuit 201 can be coupled to the sensor components 104, 105, 105' using a plurality of sensor component flexures. In the embodiment shown, the flexible circuit 201 is coupled to the driver 104 using first and second driver flexures 210, 210'. Likewise, the flexible circuit 201 is coupled to the pick-off sensors 105, 105' using first and second pick-off flexures 211, 211' and 212, 212', respectively. The flexures may comprise a similar configuration as the main body 202 of the flexible circuit 201. However, the flexures may be limited to including electrical traces for the particular sensor component being coupled while the main body 202 can include substantially all of the electrical traces required. According to an embodiment, the flexures can comprise integral components to the main body 202 of the flexible circuit 201. As shown, the flexures can extend from the main body 202. Therefore, the flexures do not require separate soldering joints as required between the wire leads and the PCBs of the prior art sensor assembly 10. Rather, the flexures only need to be coupled to the associated sensor component. The flexures can provide both physical and electrical coupling between the flexible circuit 201 and the sensor components. As can be appreciated, unlike prior art wire leads that are susceptible to differences in length as the wire leads are being soldered to the sensor components and the PCB, the flexures can comprise an integral component of the flexible circuit 201. The flexible circuit 201, including the flexures, can be formed in a reproducible manner with substantially uniform size and length from one flexible circuit to another.

It should be appreciated, that although not shown in FIG. 2, in some embodiments, the flexible circuit 201 may include a plurality of electrical resistors, similar to the resistors 115 shown in FIG. 1, in order to regulate the power delivered to the sensor components.

Figure 3:
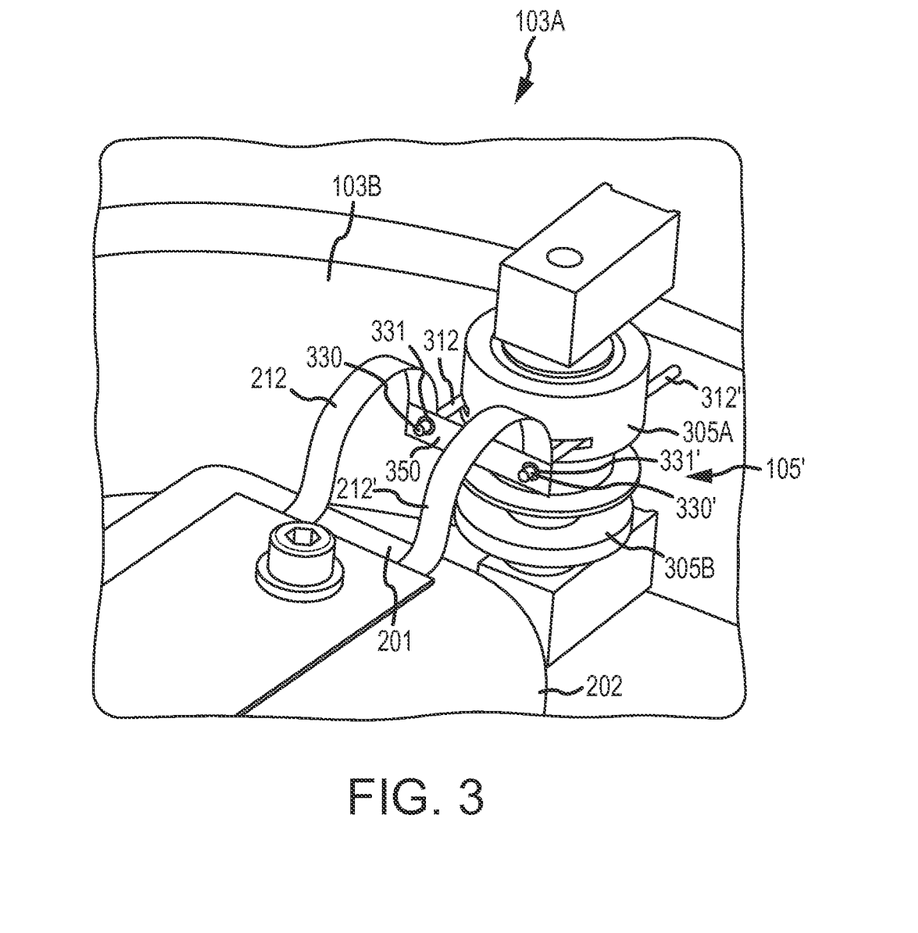
FIG. 3 shows the flexible circuit coupled to a sensor component of the sensor assembly according to an embodiment.

FIG. 3 shows a more detailed view of the coupling between the flexible circuit 201 and a sensor component. In the embodiment shown in FIG. 3, the sensor component comprises the second pick-off sensor 105'. However, it should be appreciated that similar couplings can be made to the other sensor components, i.e., the driver 104, the first pick-off sensor 105, and the RTD.

According to the embodiment shown, the pick-off sensor 105' comprises a coil/magnet configuration with the pick-off coil 305A coupled to the first flow conduit 103A and the pick-off magnet 305B coupled to the second flow conduit 103B. It should be appreciated, however, that other types of drivers and pick-off sensors may be used, such as optical, piezoelectric, etc. Therefore, the embodiments described should not be limited to electromagnetic sensor components; rather, coil/magnet configurations are referred to in the present description to maintain consistency.

As shown, the first and second pick-off flexures 212, 212' are coupled to first and second sensor component pins 312, 312'. Therefore, the coupling of the first and second pick-off flexures 212, 212' has replaced the coupling of the wire leads 112, 112' to the first and second pins 312, 312' of the coil seen in the prior art sensor assembly 10 shown in FIG. 1. According to an embodiment, the coupling between the first and second pick-off flexures 212, 212' and the first and second pins 312, 312' can be accomplished by soldering the flexures 212, 212' to the first and second pins 312, 312'. More specifically, the flexures 212, 212' can include coupling apertures 330, 330' that are sized and shaped to receive at least a portion of the first and second pins 312, 312' of the coil 305A. The coupling apertures 330, 330' can comprise electrically conductive portions that allow suitable electrical communication between the traces (See FIGS. 5 & 6) of the first and second flexures 212, 212' and the first and second pins 312, 312' of the coil 305A. However, those skilled in the art can readily appreciate alternative configurations. The coupling between the flexures 212, 212' and the pins 312, 312' provides an electrical as well as physical coupling between the flexible circuit 201 and the pick-off sensor 105'.

While soldering may provide sufficient coupling in some circumstances, as mentioned above, in some higher temperature applications, soldered joints can be compromised as the soldering material can melt. Therefore, in some situations, soldering the coil pins 312, 312' directly to the flexures 212, 212' may result in a limited temperature range for the sensor assembly 200. Therefore, according to an embodiment, the flexures 212, 212' can be provided with tubular rivets 331, 331'. The tubular rivets 331, 331' are shown surrounding the coupling apertures 330, 330 in FIG. 3 and are shown in greater detail in the cross-sectional view shown in FIG. 7.

According to an embodiment, the first and second flexures 212, 212' are also coupled to one another via a redundant redundancy flexure 350. The redundant flexure 350 can create a redundant circuit as explained in more detail below. The redundant redundancy flexure 350 provides a completed electrical circuit even in the event that one of the flexures 212, 212' is broken.

The configuration shown in FIG. 3 reduces the stress applied to the soldered joint compared to the prior art situation. The flexures 212, 212' are more flexible than the prior art wire leads, thereby reducing the stress created as the flow conduits 103A, 103B vibrate. Additionally, the flexures 212, 212' comprise an integrally formed portion of the flexible circuit 201 resulting in more uniform and reproducible lengths for the flexures 212, 212' than was possible for the independent wire leads shown in FIG. 1. However, while the flexures 212, 212' shown in FIG. 3 reduce the physical stress on the solder joints, the solder joints may still experience some strain in order to retain the first and second contacts 312, 312' within the coupling apertures 330, 330' as the conduits 103A, 103B vibrate.

Figure 4:
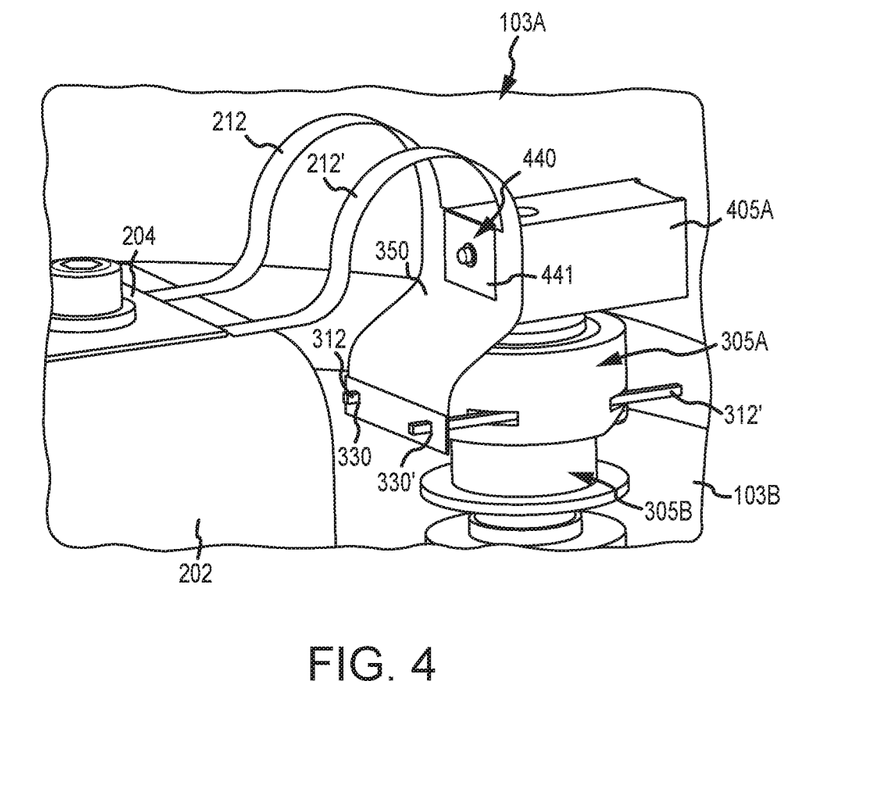
FIG. 4 shows the flexible circuit coupled to the sensor component according to another embodiment.

FIG. 4 shows the flexures 212, 212' coupled to a sensor component according to another embodiment. In the embodiment shown in FIG. 4, the flexures 212, 212' are coupled to a strain relief 440. According to an embodiment, the strain relief 440 can comprise a portion of the coil 305A. More specifically, the stain relief 440 can be formed on a conduit bracket 405A of the coil 305A. According to another embodiment, the strain relief 440 can be coupled to a portion of the coil 305A. In the embodiment shown, the strain relief 440 is coupled to the redundant flexure 350 that joins the flexures 212, 212'. The redundant flexure 350 is shown slightly larger in the embodiment of FIG. 4 than in the embodiment shown in FIG. 3 in order to accommodate the strain relief 440. However, the stain relief 440 does not have to be coupled to the redundant flexure 350 and may be coupled to the first and second flexures 212, 212'. A strain relief as shown in FIG. 4 was not feasible in the prior art because contact with the wire leads could cause a short circuit. However, the flexible circuit 201 comprises the insulating substrate that can prevent or substantially reduce the risk of a short circuit. Consequently, the strain relief 440 can be used.

With the stain relief 440 coupled to the flexures 212, 212', the solder joints at the coupling apertures 330, 330' and the first and second coil pins 312, 312' experience a substantially reduced amount of strain. This is because, as the flow conduits 103A, 103B vibrate, the relative position between the stain relief 440 and the contacts 312, 312' remain stationary. In other words, the relative position of the portion of the flexures 212, 212' coupled to the strain relief 440 and the first and second contacts 312, 312' remains substantially constant, even during vibration of the conduits 103A, 103B. Consequently, during vibrations, the coupling between the coupling apertures 330, 330' and the first and second pins 312, 312' are not subject to pulling or any other type of deformation. Rather, the pulling and deformation is experienced between the strain relief and the mounting plate 204. As can be appreciated, because the flexures 212, 212' comprise part of the flexible circuit, which is capable of deformation, the vibrations, and excessive movements are easily accommodated.

According to the embodiment shown, the strain relief 440 comprises a plate 441 that can be coupled to the conduit bracket 405A of the sensor component 305A with the flexures 212, 212', and more specifically, the redundant flexure 350 sandwiched between the plate 441 and the conduit bracket 405A. While a single plate 441 is shown, it should be appreciated that in other embodiments, the flexures 212, 212' may not be joined with the redundant flexure 350 and thus, multiple plates can be provided. Furthermore, while the stain relief 440 of the presently described embodiment utilizes a plate 441, it should be appreciated that other configurations may be used to couple a portion of the flexures 212, 212' to the conduit bracket 405A. For example, the redundant flexure 350 may be coupled to the conduit bracket 405A using an adhesive, clip, projection and corresponding aperture, etc. Advantageously, the strain relief 440 can extend the life of the sensor assembly 200, and in particular the life of the coupling between the flexible circuit 201 and the various sensor components.

As mentioned briefly above, the flexible circuit 201 of the present embodiment can include redundant circuitry. The redundant circuitry allows power, signals, and/or ground to be delivered between the meter electronics 20 and the sensor components even if one of the flexures to the sensor component is broke.

Figure 5:
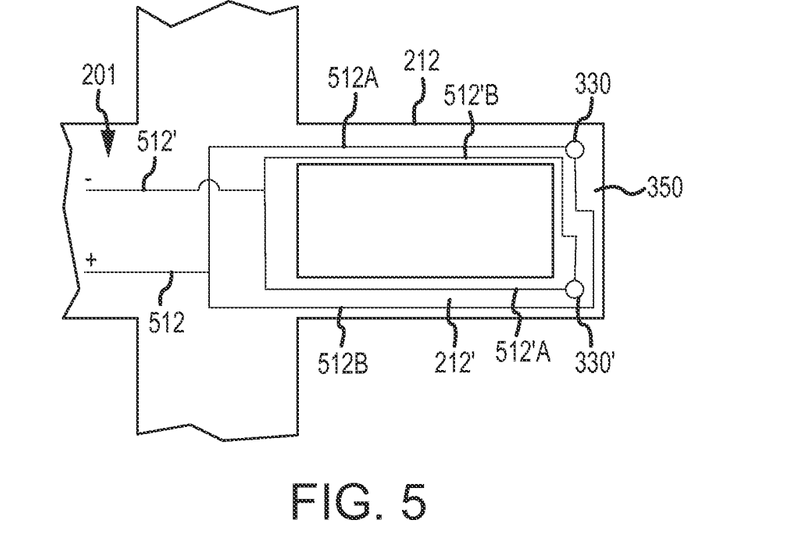
FIG. 5 shows a sensor component flexure of the flexible circuit according to an embodiment.

FIG. 5 shows a cross-sectional view of the flexures 212, 212' according to an embodiment. As shown in FIG. 5, the flexible circuit 201 includes two electrical traces 512 and 512'. The electrical traces 512, 512' can provide electrical communication between a sensor component, such as the pick-off sensor 105' and the meter electronics 20, for example. In some embodiments, the electrical traces 512, 512' may provide electrical communication between a sensor component and another intermediary electrical component, such as the leads 130, for example. Therefore, while only two electrical traces 512, 512' are shown, those skilled in the art will readily recognize that two or more traces can be provided for each of the sensor components coupled to the flexible circuit 201.

According to the embodiment shown, one of the electrical traces can comprise a reference voltage, such as ground, and the other electrical trace can be at some voltage different than reference voltage as indicated by the + and − signs. As shown, both of the electrical traces 512, 512' extend through each of the flexures 212, 212' as well as the redundant flexure 350. The first electrical trace 512 separates into a primary trace 512A that extends through the flexure 212 and a redundant trace 512B that extends through the flexure 212' and the redundant flexure 350 to provide electrical communication to the first coupling aperture 330. Similarly, the second electrical trace 512' separates into a primary electrical trace 512'A that extends through the flexure 212' and a redundant electrical trace 512'B that extends through the flexure 212 and the redundant flexure 350 to provide electrical communication to the second coupling aperture 330'. As those skilled in the art will understand, power and/or signals can travel from either or both of the primary first electrical trace 512A and the redundant first electrical trace 512B to the first coupling aperture 330. With the electrical contact 312 of the coil 305A coupled to the first coupling aperture 330, the power can flow through the coil 305A towards the second coupling aperture 330'. The primary second electrical trace 512'A and/or the redundant second electrical trace 512'B can complete the circuit.

Figure 6:
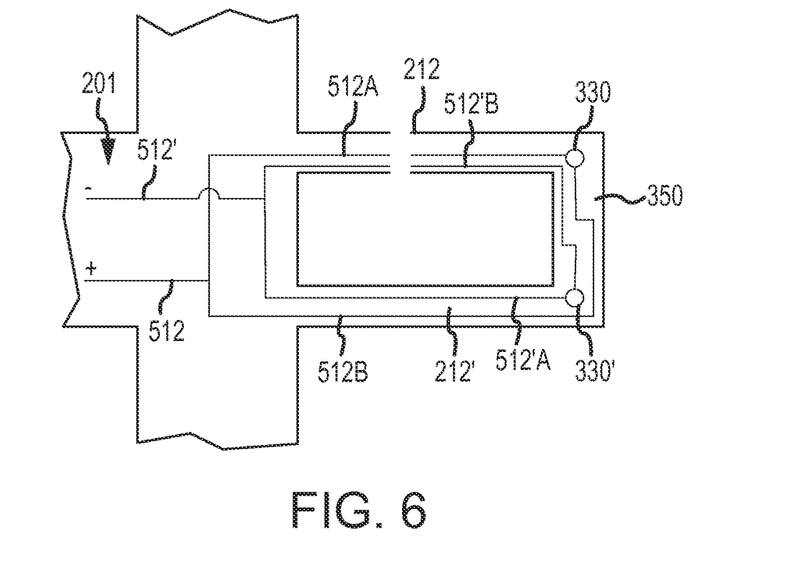
FIG. 6 shows the sensor component flexure of the flexible circuit according to another embodiment.

FIG. 6 shows a portion of the flexible circuit 201 according to another embodiment. In the embodiment shown in FIG. 6, the first flexure 212 has been broken. The flexure 212 may have broken for a number of reasons. As can be appreciated, if the wire lead 112 of the prior art sensor assembly 10 broke in a similar manner to the flexure 212, no power or signal could be communicated to the pick-off sensor 105'. However, because the traces 512, 512' extend through both flexures 212, 212' and not just one of the flexures 212, 212', the broken flexure 212 does not prevent power and/or signals to be communicated to the pick-off sensor 105' as the other flexure can provide the electrical communication path. With the first flexure 212 broken, power and/or signals can be communicated through the redundant first electrical trace 512B and the primary second electrical trace 512'A. Therefore, the embodiment shown that includes the redundant flexure 350 creates a redundant circuit to allow continued use after one of the flexures breaks. Consequently, the sensor component can communicate with the meter electronics 20 with a single flexure 212 or 212' and the redundant flexure 350.

Figure 7:
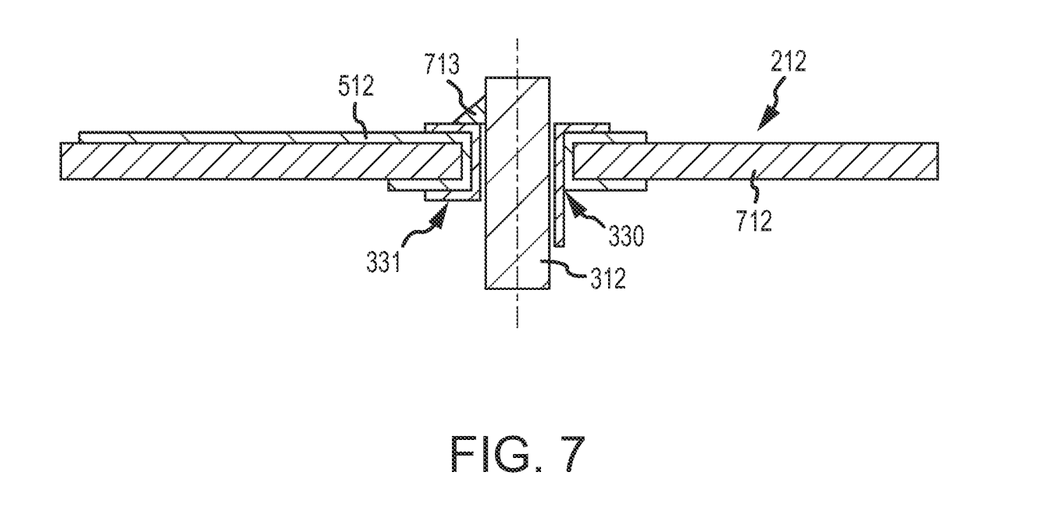
FIG. 7 shows a cross-sectional view of a flexure coupled to a coil pin using a tubular rivet according to an embodiment.

FIG. 7 shows a cross-sectional view of the coil pin 312 received by the coupling aperture 330 according to an embodiment. Although the cross-sectional view only shows a single flexible substrate 712, it should be appreciated that as discussed above, the electrical trace 512 may be sandwiched between two flexible substrates. As mentioned above, in some embodiments, soldering the traces 512, 512' directly to the coil pins 312, 312' can limit the temperature range of the sensor assembly 200 as the solder may melt below an intended operating temperature. However, using higher heat coupling techniques directly on the electrical traces 512, 512' may cause permanent damage to the traces 512, 512'. Consequently, according to an embodiment, the sensor assembly 200 can use tubular rivets 331, 331'. The tubular rivet 331 is shown in FIG. 7; however, it should be appreciated that similar tubular rivets may be provided for each of the coupling apertures of the flexible circuit 201.

According to an embodiment, at least a portion of the tubular rivet 331 can be inserted into the coupling aperture 330. The right side of FIG. 7 shows the tubular rivet 331 prior to being bucked (deformed) and welded to the coil pin 312. The left side of FIG. 7 shows the tubular rivet 331 inserted, bucked, and welded or otherwise coupled to the coil pin 312 to electrically and physically couple the flexure 212 to the coil pin 312. According to an embodiment, the portion of the rivet 331 that is received in the coupling aperture 330 (rivet tail) can be slightly larger than the coupling aperture so as to partially deform upon insertion. This can ensure adequate electrical contact between the rivet 331 and the electrical trace 512 and reduce the risk of electrical arcing. Once the rivet 331 is inserted through the coupling aperture 330, the rivet can be bucked into the form shown on the left of FIG. 7. As can be appreciated, once the rivet 331 is bucked, the rivet 331 is substantially permanently coupled to the flexure 212.

With the rivet 331 in place, at least a portion of the coil pin 312 can be inserted through the tubular rivet 331. As can be appreciated, in embodiments that utilize the rivet 331, the coupling aperture 330 needs to be slightly larger to accommodate the area occupied by the rivet 331 and still accept the coil pin 312. According to an embodiment, the rivet 331 is not as sensitive to heat as the electrical trace 512 may be. Therefore, rather than soldering the rivet 331 to the coil pin 312, the two components can be coupled together using a higher temperature process, such as spot welding, for example, as shown by the weld joint 713. Spot welding the rivet 331 to the coil pin 312 creates a higher temperature bond that can withstand higher temperature environments than soldering, for example. Additionally, spot welding can restrict the heat that is applied to the electrical trace 512 as the rivet 331 is coupled to the coil pin 312. Furthermore, as long as the rivet 331 is formed from an electrically conductive material, the rivet 331 can communicate electrical energy between the electrical trace 512 and the coil pin 312.

The embodiments described above provide an improved electrical configuration for a sensor assembly 200. While prior art sensor assemblies rely upon wire leads and multiple PCBs, the embodiments described above have reduced most of these components. The sensor assembly 200 described above utilizes a flexible circuit 201 that can be coupled to the one or more sensor components. The flexible circuit 201 can provide electrical communication between the meter electronics 20 and the sensor components. Advantageously, the flexible circuit 201 can eliminate the number of components required to provide electrical communication to the sensor components compared to the prior art sensor assembly 10. Furthermore, because the sensor component flexures can comprise integral components to the main body 202 of the flexible circuit 201, the electrical configuration is more uniform and repeatable than prior art approaches.

Additionally, as described above, the flexible circuit 201 can provide redundant circuitry in order to continue to provide electrical communication even if a sensor component flexure breaks. Furthermore, with the use of rivets received by the sensor component flexures, the sensor assembly 200 can withstand higher temperature environments than prior art sensor assemblies that utilize solder joints.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments of, and examples for, the sensor assembly are described herein for illustrative purposes, various equivalent modifications are possible within the scope of the present description, as those skilled in the relevant art will recognize. The teachings provided herein can be applied to other sensor assemblies, and not just to the embodiments described above and shown in the accompanying figures. Accordingly, the scope of the embodiments described above should be determined from the following claims.

What is claimed is:

1. A method for assembling a sensor assembly, comprising steps of:
    positioning a conduit within a case;
    coupling a sensor component to the conduit, the sensor component including one or more of a driver, a first pick-off sensor, and a second pick-off sensor;
    positioning a flexible circuit within the case; and
    coupling two sensor component flexures extending from a body of the flexible circuit to the sensor component, wherein a redundant flexure couples ends, distal from the body of the flexible circuit, of the sensor component flexures, and wherein the sensor component flexures and the redundant flexure each comprise a primary electrical trace and a redundant electrical trace, wherein the primary electrical trace and the redundant electrical trace are each disposed between at least two flexible substrates;
    coupling at least one of the sensor component flexures to a strain relief and a sensor component pin such that a portion of the sensor component flexure between and proximate to the strain relief and the sensor component pin substantially stationary, relative to the sensor component pin, during vibration of the conduit, wherein a coil of the sensor component is coupled to the strain relief.

2. The method of claim 1, further comprising coupling the flexible circuit to a meter electronics to provide electrical communication between the meter electronics and the sensor component.

3. The method of claim 1, wherein the step of coupling at least one of the sensor component flexures to the strain relief comprises inserting the sensor component pin extending from the sensor component into one or more coupling apertures.

4. The method of claim 3, further comprising a step of inserting a tubular rivet into the one or more coupling apertures.

5. The method of claim 4, further comprising a step of coupling the tubular rivet to the sensor component pin.

6. The method of claim 1, wherein the strain relief comprises a plate and the step of coupling at least one of the sensor component flexures to the strain relief comprises positioning a portion of the at least one of the sensor component flexures between the plate and a conduit bracket of the sensor component.

* * * * *

UNITED STATES PATENT AND TRADEMARK OFFICE
CERTIFICATE OF CORRECTION

PATENT NO. : 10,571,323 B2
APPLICATION NO. : 14/827536
DATED : February 25, 2020
INVENTOR(S) : Christopher A Werbach and Allan L Samson Page 1 of 1

It is certified that error appears in the above-identified patent and that said Letters Patent is hereby corrected as shown below:

In the Specification

Column 7, Lines 60-61 and 63, replace "redundant redundancy flexure 350" with --redundant flexure 350--

Signed and Sealed this
Seventh Day of July, 2020

Andrei Iancu
*Director of the United States Patent and Trademark Office*